(12) United States Patent
Song et al.

(10) Patent No.: US 8,404,277 B2
(45) Date of Patent: Mar. 26, 2013

(54) MATRIX-TYPE TRANSDERMAL DRUG DELIVERY SYSTEM AND PREPARATION METHOD THEREOF

(75) Inventors: Jin-Deok Song, Daejeon (KR); Dong-Won Kim, Daejeon (KR)

(73) Assignee: Samyang Biopharmaceuticals Corporation, Seoul (KR)

( * ) Notice: Subject to any disclaimer, the term of this patent is extended or adjusted under 35 U.S.C. 154(b) by 403 days.

(21) Appl. No.: 12/602,256

(22) PCT Filed: Jun. 5, 2008

(86) PCT No.: PCT/KR2008/003166
§ 371 (c)(1),
(2), (4) Date: Nov. 30, 2009

(87) PCT Pub. No.: WO2008/150120
PCT Pub. Date: Dec. 11, 2008

(65) Prior Publication Data
US 2010/0172946 A1    Jul. 8, 2010

(30) Foreign Application Priority Data
Jun. 8, 2007 (KR) .................. 10-2007-0056299

(51) Int. Cl.
*A61K 9/50* (2006.01)
*A61K 9/14* (2006.01)
*A61K 31/16* (2006.01)
*A01N 37/18* (2006.01)

(52) U.S. Cl. ........ 424/499; 424/484; 424/487; 514/625; 514/627

(58) Field of Classification Search ................ 424/499, 424/484, 487; 514/625, 627
See application file for complete search history.

(56) References Cited

U.S. PATENT DOCUMENTS

| | | | |
|---|---|---|---|
| 5,178,879 A | 1/1993 | Adekunle et al. | |
| 5,318,960 A * | 6/1994 | Toppo .......................... | 514/159 |
| 5,562,917 A * | 10/1996 | Durif et al. ..................... | 424/447 |
| 5,910,512 A | 6/1999 | Conant | |
| 6,348,501 B1 | 2/2002 | Holt et al. | |
| 6,593,370 B2 | 7/2003 | Tamura et al. | |
| 7,691,404 B2 * | 4/2010 | Song et al. ..................... | 424/448 |
| 2003/0072792 A1 * | 4/2003 | Flanigan et al. ............... | 424/449 |
| 2003/0170296 A1 * | 9/2003 | Sintov et al. .................. | 424/449 |
| 2004/0033254 A1 * | 2/2004 | Song et al. ..................... | 424/449 |
| 2004/0202707 A1 | 10/2004 | Muller | |
| 2006/0078603 A1 * | 4/2006 | Nguyen ......................... | 424/449 |
| 2006/0148903 A1 * | 7/2006 | Burch et al. ................... | 514/627 |
| 2007/0053965 A1 | 3/2007 | Kugelmann et al. | |

FOREIGN PATENT DOCUMENTS

| | | |
|---|---|---|
| CN | 101084883 | 12/2007 |
| KR | 10-1999-0029556 | 4/1999 |
| KR | 10-2000-0024702 | 5/2000 |
| KR | 10-2002-0066047 | 8/2002 |
| WO | WO-2004/021990 A2 | 3/2004 |
| WO | WO-2004/047820 A1 | 6/2004 |
| WO | WO-2007/100910 | 9/2007 |

OTHER PUBLICATIONS

Merriam Webster Online Dictioanry, obtained onlin at: http://www.merriam-webster.com/cgi-bin/dictionary?book=Dictioanry&va-derivative, obtained online at Jul. 5, 2008.*
Wermuth, Drug Disovery Today, 2006, 11(7/8), 348-354.*
International Search Report and Written Opinion mailed Oct. 13, 2008. PCT/KR2008/003166.
Babbar et al., Pharmacokinetic Analysis of Capsaicin after Topical Administration of a High-Concentration Capsaicin Patch to Patients With Peripheral Neuropathic Pain. Ther Drug Monit., vol. 31, No. 4, Aug. 2009, pp. 502-510.
NGX-4010, a high-concentration capsaicin patch, for the treatment of postherpetic neuralgia: a randomised, double-blind study. www.thelancet.com/neurology, vol. 7, Dec. 2008, pp. 1106-1112.
Wu et al., Development and evaluation of transdermal patches of nonivamide and sodium nonivamide acetate. Kaohsiung Medical College, pp. 135-138, 1997.
Simpson et al., Controlled trial of high-concentration capsaicin patch for treatment of painful HIV neuropathy, Mount-Sinai School of Medicine, pp. 2305-2313, 2008.
Malmberg et al., Reduced heat sensitivity and epidermal nerve fiber immunostaining following single applications of high-concentration capsaicin patch., International Association for the Study of Pain, pp. 360-367, 2004.
Noto at al., NGX-4010, a high-concentration capsaicin dermal patch for lasting relief of peripheral neuropathic pain. Current Opinion in Investigational Drugs, 2009, pp. 702-710.
Chanda et al., Developmental Toxicity Study of Pure trans-Capsaicin in Rats and Rabbits, International Journal of Toxicology, 25;205-217, 2006.

* cited by examiner

*Primary Examiner* — Abigail Fisher
(74) *Attorney, Agent, or Firm* — Gifford, Krass, Sprinkle, Anderson & Citkowski, P.C.

(57) ABSTRACT

A matrix-type transdermal drug delivery system including capsaicin or a capsaicin derivative as an active component and used for treating neuropathy, pain, and inflammation and a preparation method thereof are provided. The matrix-type transdermal drug delivery system includes: a drug protecting layer; a matrix layer formed on the drug protecting layer and including 0.1-25 wt % of capsaicin or a capsaicin derivative, 40-95 wt % of an adhesive including a water-insoluble acrylic polymer, 1-30 wt % of an alcohol having a molecular weight of 600 Daltons or less, 0.1-20 wt % of a nonionic surfactant, and 0.1-20 wt % of a solubilizing agent including a hydrophilic polymer; and a release liner formed on the matrix layer, and is used for treating neuropathy, pain, or inflammation.

15 Claims, 2 Drawing Sheets

MATRIX-TYPE TRANSDERMAL DRUG DELIVERY SYSTEM AND PREPARATION METHOD THEREOF

CROSS-REFERENCE TO RELATED APPLICATIONS

This application is the U.S. national phase of PCT/KR2008/003166 filed Jun. 5, 2008, which claims priority of Korean Patent Application No. 10-2007-0056299 filed Jun. 8, 2007.

BACKGROUND OF THE INVENTION (a) Field of the Invention

The present invention relates to a matrix-type transdermal drug delivery system including capsaicin or a capsaicin derivative as an active component and that is used for treating neuropathy, pain, or inflammation, and a preparation method thereof.

(b) Description of the Related Art

The present invention relates to a matrix-type transdermal drug delivery system including capsaicin or a capsaicin derivative as an active component and that is used for treating neuropathy, pain, or inflammation, and a preparation method thereof. More particularly, the present invention relates to a matrix-type transdermal drug delivery system that is capable of enhancing skin permeability and extending the medical efficacy maintaining time of the capsaicin or the capsaicin derivative, that is, the active component. The present invention also relates to a preparing method of the matrix-type transdermal drug delivery system that is capable of preparing the matrix-type transdermal drug delivery system more easily in a short time.

Capsaicin is the active component of hot peppers that causes a spicy taste, and it is represented by the chemical name N-(4-hydroxy-3-methoxybenzyl)-8-methylnon-6-enamide). It is known that the capsaicin stimulates pain neurons of the sensory nerves and causes pain, and releases various mediators of inflammation at the early stage of administration, but its continuous administration incapacitates the neurons and brings an insensible state to other external stimulators as well as to the capsaicin. Such action of the capsaicin is called desensitization.

It is also known that the analgesic effect due to such desensitization is different from the analgesic effect of other anodynes in its functional mechanisms, and the analgesic effect is as strong as morphine. Furthermore, it is known that the capsaicin may be effectively used for treating neuropathy or inflammation. However, the capsaicin shows a stimulation effect at the early stage of oral administration, and it may give rise to hypothermia, contraction of the bronchial tube, increase of gastrointestinal activity, side effects to the cardiovascular system, such as hypotonia, or side effects to the respiratory system.

To inhibit such side effects due to the oral administration of the capsaicin, various studies for formulating the capsaicin into a transdermal medicine have been carried out. Representatively, products that are fabricated as ointments have come on the market, and studies for formulating the same into a transdermal medicine, i.e., a patch, are now under way.

Technologies regarding topical functional medicines, such as ointments, are disclosed in U.S. Pat. Nos. 5,178,879, 5,910, 512, 6,348,501, and 6,593,370. Particularly, the technologies disclosed in the patents are mainly related to medical compositions, such as gels, lotions, or ointments, and the medical compositions are directly used on skin without a drug protecting layer that seals the active components. However, when the capsaicin is formulated into an ointment and the like, without the drug protecting layer, its smell stimulates the respiratory system and may cause similar side effects to the case of the oral administration, because the volatility of the capsaicin is relatively high. Furthermore, when the capsaicin is formulated into an ointment and the like, it is required to rub the ointment three or four times or more a day by hand, because the skin permeability of the capsaicin may be reduced and the medical efficacy maintaining time is shortened. Further, the capsaicin remains on the hand, and therefore it may unnecessarily cause stimulation or pain, and it also may cause inconvenience in that clothes are stained by the ointment. Especially, such inconvenience increases because it is required to rub the ointment for a long time for treating pain and the like by using the capsaicin.

In addition, a patch including a drug protecting layer, a polysiloxane-based layer including capsaicin, diethyleneglycol monoethyl ether, ethyl cellulose, and a silicone oil is disclosed in U.S. Publication No. 2004/0202707.

Furthermore, a method of eliminating capsaicin remaining on the skin by using a cleansing gel after using a patch including capsaicin in a large quantity on the skin and removing the patch is disclosed in PCT publication No. WO04/021990. In such method, the capsaicin of a large quantity may stimulate the skin severely, and it is inconvenient in that the skin must be separately cleaned by using a cleansing gel after removing the patch. Furthermore, the medical efficacy maintaining time cannot be increased sufficiently, even though the capsaicin is formulated into the patch.

SUMMARY OF THE INVENTION

The present invention is to provide a matrix-type transdermal drug delivery system that is capable of enhancing skin permeability of capsaicin or a capsaicin derivative, the active component, and extending the medical efficacy maintaining time of the active component.

Another aspect of the present invention is to provide a preparing method of the matrix-type transdermal drug delivery system that is capable of preparing the matrix-type transdermal drug delivery system more easily in a short time.

DETAILED DESCRIPTION OF THE PREFERRED EMBODIMENTS

Figure 1:
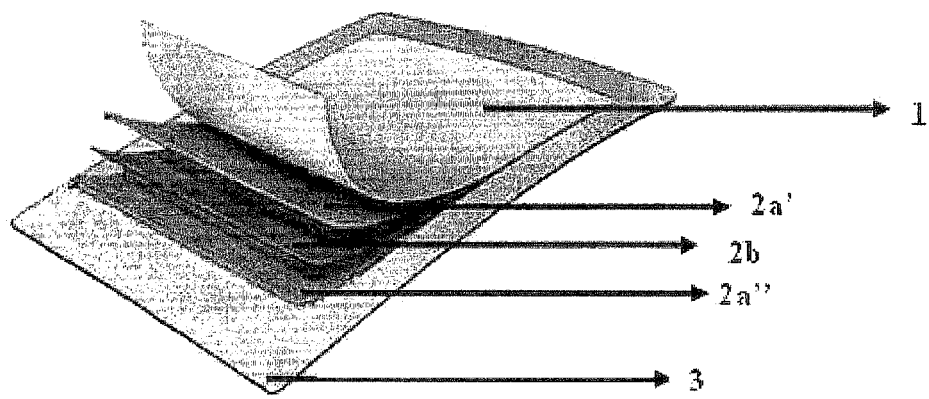
FIG. 1 is a schematic sectioned drawing of the matrix-type transdermal drug delivery system according to an embodiment of the present invention.

The technical aspects of the present invention are not limited to or by the above-mentioned technical aspects, and other technical aspects that are not mentioned above can be clearly understood by a person skilled in the art from the following description.

According to an embodiment of the present invention, a matrix-type transdermal drug delivery system used for treating neuropathy, pain, or inflammation, and including: a drug protecting layer; a matrix layer formed on the drug protecting layer, and including 0.1-25 wt % of capsaicin or a capsaicin derivative, 40-95 wt % of an adhesive including a water-insoluble acrylic polymer, 1-30 wt % of an alcohol having a molecular weight of 600 Daltons or less, 0.1-20 wt % of a nonionic surfactant, 0.1-20 wt % of a solubilizing agent including a hydrophilic polymer; and a release liner formed on the matrix layer, is provided.

Hereinafter, the matrix-type transdermal drug delivery systems according to the embodiments of the present invention are explained in more detail.

The matrix-type transdermal drug delivery system according to one embodiment of the present invention basically includes a drug protecting layer, a matrix layer, and a release liner laminated in order.

In such laminated structure of the matrix-type transdermal drug delivery system, the drug protecting layer plays a role of preventing the active components from staining clothes or volatilizing and vanishing, by covering the matrix layer including the active components (the drugs). The drug protecting layer may preferably include a film or a nonwoven fabric consisting of polyester, polyurethane, polyethylene, or rayon. Since the transdermal drug delivery system includes the capsaicin or the capsaicin derivative as the active component and is used for treating neuropathy, pain, or inflammation, the transdermal drug delivery system for such use is easily applied to a bending part of a body, such as a joint, a finger, or a toe. The matrix-type transdermal drug delivery system can be adequately applied to various bending parts of a body because the drug protecting layer includes the film or the nonwoven fabric consisting of said materials.

In the laminated structure, furthermore, the release liner is a layer that covers and protects the matrix layer including the active component until the matrix-typed transdermal drug delivery system is used, and is eliminated just before the matrix-typed transdermal drug delivery system is attached to the skin. The release liner may include a drug impermeable film that is conventionally used for a release liner release liner of a matrix-type transdermal drug delivery system, for example, a patch.

Furthermore, the matrix layer formed between the drug protecting layer and the release liner includes the following various components including the active component.

Firstly, the matrix layer includes the capsaicin or the capsaicin derivative as the active component. The matrix-type transdermal drug delivery system can be used for treating neuropathy, pain, or inflammation, because the matrix layer includes such active component.

The active component, that is, the capsaicin or the capsaicin derivative, may include any capsaicin-based material that is usable for treating neuropathy, pain, or inflammation. For example, the capsaicin or the capsaicin derivative may include one material or a mixture of two or more materials selected from the group consisting of capsaicin, dihydrocapsaicin, nordihydrocapsaicin, homodihydrocapsaicin, homocapsaicin, capsazepine, N-vanillylnonanamide, (Z)-capsaicin, (E)-capsaicin, and 6-iodonordihydrocapsaicin.

The capsaicin or the capsaicin derivative can be included with a content of 0.1-25 wt %, and preferably with a content of 0.5-10 wt %, among the components forming the capsaicin layer. When the content of the capsaicin or the capsaicin derivative is below 0.1 wt %, it is difficult to have it work properly, because the skin permeability excessively decreases due to the decrease of the concentration of the active component, and when the content is over 25 wt %, it may not be properly dissolved into the transdermal drug delivery system and may be extracted.

Furthermore, the matrix layer includes the following components in addition to the capsaicin or the capsaicin derivative.

The matrix layer includes an adhesive including a water-insoluble acrylic polymer. The acrylic polymer is superior in terms of adhesive power and adhesive durability in comparison with a water-soluble polymer used in a conventional plaster as an adhesive. Since the capsaicin or the capsaicin derivative is practically insoluble in water and has a low melting point (60-65° C.), it is preferable to include the water-insoluble acrylic polymer as an adhesive. The reason is that the capsaicin or the capsaicin derivative is more soluble in the organic solvent in which the water-insoluble acrylic polymer is dissolved, and thus it is possible to increase the concentration of the active component much more in the matrix layer by using the water-insoluble acrylic polymer as an adhesive. Accordingly, the skin absorptance (the skin permeability) can be increased by raising the concentration of the active component in the transdermal drug delivery system, and it is also possible to show superior medical effects or characteristics, even it is applied to the skin for 1 day or more, and preferably 3 days or more, because the adhesive power is also good. Furthermore, by using the adhesive including the water-insoluble acrylic polymer having good adhesive durability, it is also possible to lessen the amount of the adhesive used and to reduce the thickness of the transdermal drug delivery system to 30-300 μm, and preferably to 100-200 μm, and the adhering feeling of the transdermal drug delivery system is good even when it is applied to a bending part of the body for a long time.

The water-insoluble acrylic polymer, for example, may include a homopolymer or a copolymer polymerized from one or more monomers selected from the group consisting of 2-ethylhexylacrylate, vinylacrylate, and vinylacrylic acid, and may further include any homopolymer or copolymer polymerized from various acrylic monomers in addition to the monomers, without limitation. Furthermore, the adhesive may include the water-insoluble acrylic polymer alone or may further include other polymers used as an adhesive for a matrix-type transdermal drug delivery system together. For example, a natural or synthetic rubber such as a vinylacetate-based polymer, a polyisobutylene, a neoprene, a polybutadien, a polyisoprene, and the like, and an ethylenevinylacetate-based copolymer, a polysiloxane, a polyacrylate, or a polyurethane, and the like, can be included in company with the water-insoluble acrylic polymer.

The adhesive including the water-insoluble acrylic polymer is included in the matrix layer with a content of 40-95 wt %, and preferably with a content of 45-85 wt %. When the content of the adhesive is below 40 wt %, it is difficult for the matrix layer and the matrix-type transdermal drug delivery system including the matrix layer to have proper adhesive power to the skin, and when the content is over 95 wt %, it is difficult to include the other components of the matrix layer with an effective content.

The matrix layer also includes the alcohol having a molecular weight of 600 Daltons or less, the nonionic surfactant, or a mixture thereof, as a skin permeation enhancer. The capsaicin or the capsaicin derivative, the active component, shows high solubility in the alcohol having low molecular weight of 600 Daltons or less. Therefore, the active component stays in the matrix layer with high solubility in the alcohol, and slowly migrates toward the skin according to the concentration difference of the active component, and, at this time, the nonionic surfactant quickens the migration of the active component toward the skin. Hence, the skin permeability of the active component can be greatly improved and the medical efficacy maintaining time can be extended to 1 day or more, preferably to 3 days or more, and to a maximum of 7 days, when the matrix-type transdermal drug delivery system is attached to the skin, because the alcohol and the nonionic surfactant, the skin permeation enhancers, are included in the matrix layer.

In the skin permeation enhancers, the alcohol may include a $C_1$-$C_{12}$ alcohol(s) having a molecular weight of 600 Daltons or less, for example a material or a mixture of two or more materials selected from the group consisting of ethanol, isopropanol, butanol, benzylalcohol, triacetin, transcutol, propyleneglycol, glycerin, and a polyethyleneglycol having a molecular weight of 600 Daltons or less, and may preferably include propyleneglycol, triacetin, or transcutol.

On the other hand, the surfactant is generally classified as an anionic surfactant, a cationic surfactant, an amphoteric surfactant, and a nonionic surfactant, and all of the surfactants can quicken the migration of the active component toward the skin. However, it was reported that only the nonionic surfactant can reduce damage to the skin and the other surfactants may cause damage to the skin (K.A. Water, Penetration enhancers and their use in transdermal therapeutic system, Transdermal Drug Delivery, pp 212-224, Dekker, (1989); and Eagle et al., J. Toxicol. cut and Ocular toxicol, 11, 77-92 (1992)). Therefore, the matrix layer includes the nonionic surfactant as the skin permeation enhancer.

As the nonionic surfactant, for example, a material or a mixture of two or more materials selected from the group consisting of glycerol monolaurate, glycerol monooleate, glycerol monolinoleate, glycerol trilaurate, glycerol trioleate, glycerol tricaprylate, propylene glycol monolaurate, propylene glycol dilaurate, caprylic/capric triglyceride, methyl laurate, methyl caprate, isopropyl myristate, isopropyl palmitate, ethyl oleate, oleyl oleate, sorbitan monolaurate, sorbitan monooleate, polyoxyethylene lauryl ether, polyoxyethylene cetyl ether, polyoxyethylene stearyl ether, polyoxyethylene oleyl ether, polyoxyethylene stearate, polyoxyethylene-9-nonyl phenyl ether, polyethyleneglycol-40 hydrogenated caster oil, polyethyleneglycol-35 hydrogenated caster oil, octocynol-11, a fatty acid ester of Tween®, and a fatty acid ester of Span® (otherwise known as sorbitan) can be used, and preferably sorbitan monooleate, glycerol monolaurate, glycerol monooleate, or sorbitan monolaurate can be used. However, the examples are not limited to these materials, and any other nonionic surfactant can be used without limitation.

The skin permeation enhancers increase the skin permeability of the active component to a certain content in proportion to its content, but the skin permeability of the active component is not increased much at the content beyond that and the stimulation or the damage to the skin is increased. Therefore, in the skin permeation enhancers, the alcohol is included in the matrix layer with a content of 1-30 wt %, and preferably with a content of 5-25 wt %, and the nonionic surfactant is included in the matrix layer with a content of 0.1-20 wt %, and preferably with a content of 1-15 wt %.

Furthermore, the skin permeation enhancers, i.e., the nonionic surfactant and the alcohol, may be included in the weight ratio of the nonionic surfactant to the alcohol at 1:1 to 1:4 in the matrix layer. It is possible to improve the skin permeability and the medical efficacy maintaining time of the active component still more while reducing the stimulation or damage of the skin, and therefore the skin permeation enhancers are included in that weight ratio.

The matrix layer further includes the solubilizing agent including the hydrophilic polymer. Such solubilizing agent plays a role of stably maintaining the concentration of the active component in the matrix layer or further improving its stability.

For example, the hydrophilic polymer included in the solubilizing agent may include a material or a mixture of two or more materials selected from the group consisting of polyvinylpyrrolidone, colloidal silicone dioxide, polyvinylalcohol, sodium carboxymethyl cellulose, hydroxyethyl cellulose, hydroxypropyl cellulose, hydroxypropyl methyl cellulose, carbopol, and poloxamer, and it may also include various hydrophilic polymers in addition to the materials without limitation, and it may preferably include one material or a mixture of two or more materials of polyvinylpyrrolidone, colloidal silicone dioxide, or poloxamer.

Furthermore, the solubilizing agent is included in the matrix layer with a content of 0.1-20 wt %, and preferably with a content of 1-15 wt %.

The matrix layer may be formed into a single layer or a laminated structure of two or more layers. For example, the matrix layer may be formed into a laminated structure of at least one adhesive layer and a drug containing layer, and may include the above-mentioned components separately in the layers or may include a part of the components together.

The matrix-type transdermal drug delivery system according to another embodiment of the present invention is provided hereinafter. Such matrix-type transdermal drug delivery system includes: a drug protecting layer; a first adhesive layer formed on the drug protecting layer and including the adhesive including the water-insoluble acrylic polymer; a drug containing layer formed on the first adhesive layer and including the capsaicin or the capsaicin derivative; a second adhesive layer formed on the drug containing layer and including the adhesive including the water-insoluble acrylic polymer; and a release liner formed on the second adhesive layer. At least one layer of the first adhesive layer and the second adhesive layer may further include the alcohol having a molecular weight of 600 Daltons or less, the nonionic surfactant, or the solubilizing agent including the hydrophilic polymer, and the drug containing layer may further include the alcohol having a molecular weight of 600 Daltons or less, the nonionic surfactant, or the solubilizing agent including the hydrophilic polymer. The matrix-type transdermal drug delivery system is used for treating neuropathy, pain, or inflammation by including the capsaicin and the capsaicin derivative as the active component.

Specifically, the matrix-type transdermal drug delivery system includes: a drug protecting layer; a first adhesive layer formed on the drug protecting layer and including the adhesive including the water-insoluble acrylic polymer; a drug containing layer formed on the first adhesive layer and including the capsaicin or the capsaicin derivative, the alcohol having a molecular weight of 600 Daltons or less, and the solubilizing agent including the hydrophilic polymer; a second adhesive layer formed on the drug containing layer and including the adhesive including the water-insoluble acrylic polymer; and a release liner formed on the second adhesive layer.

A schematic sectioned drawing of the matrix-type transdermal drug delivery system according to this embodiment of the present invention is illustrated in FIG. 1.

Referring to FIG. 1, the matrix-type transdermal drug delivery system includes the drug protecting layer 1, the matrix layer 2a', 2b, 2a", and the release liner 3 laminated in order, like the first embodiment of the present invention, and the drug protecting layer 1 and the release liner 3 may include the film or the nonwoven fabric consisting of said materials and the drug impermeable film, respectively.

Furthermore, the matrix layer 2a', 2b, 2a" includes the capsaicin or the capsaicin derivative as the active component, and further includes the adhesive including the water-insoluble acrylic polymer, the skin permeation enhancers of the alcohol having a molecular weight of 600 Daltons or less and the nonionic surfactant, and the solubilizing agent including the hydrophilic polymer.

Detailed explanations regarding the components are omitted hereinafter, because the details of the components were explained with regard to the first embodiment of the present invention.

In the matrix-type transdermal drug delivery system according to this embodiment of the present invention, the matrix layer 2a', 2b, 2a" includes the first adhesive layer 2a', the drug containing layer 2b, and the second adhesive layer 2a", laminated in order.

In the laminated structure, the first and second adhesive layers 2a', 2a" may include the nonvolatile components among the components of the matrix layer 2a', 2b, 2a". For example, the first and second adhesive layers 2a', 2a" include the adhesive including the water-insoluble acrylic polymer, and at least one layer of the first and second adhesive layers 2a', 2a" further include the alcohol having a molecular weight of 600 Daltons or less, the nonionic surfactant, or the solubilizing agent including the hydrophilic polymer.

Furthermore, the drug containing layer 2b mainly includes the volatile components, for example, the active component of the capsaicin or the capsaicin derivative, the alcohol having a molecular weight of 600 Daltons or less, and the solubilizing agent including the hydrophilic polymer. The drug containing layer 2b may further include the nonionic surfactant.

It is possible to easily prepare the matrix-type transdermal drug delivery system including the matrix layer 2a', 2b, 2a" in a short time, according to classifying the components into the volatile components and the nonvolatile components and including the components separately in each layer. Specifically, the matrix-type transdermal drug delivery system can be prepared by steps of coating a composition including the adhesive and the other nonvolatile components on the drug protecting layer 1 and the release liner 3, evaporating and eliminating the organic solvent included in the composition by drying so as to prepare the first and second adhesive layers 2a', 2a", and coating a composition including the volatile component (the active component) on the first adhesive layer 2a' and the second adhesive layer 2a". In this method, the drying process can be carried out at relatively high temperature in a short time without a loss of the volatile components, especially the active component, because the composition of the volatile components is separately coated after the steps of coating and drying the composition of the nonvolatile components, which does not contain the volatile components, especially the active component of the capsaicin or the capsaicin derivative. Therefore, the matrix-type transdermal drug delivery system including the matrix layer can be easily prepared in a short time.

On the other hand, the first adhesive layer 2a' or the second adhesive layer 2a" may separately include any one or two or more components of the nonionic surfactant, the alcohol, or the solubilizing agent in each layer in addition to the adhesive, or may include all of the components together in one layer, and it is also possible that only one layer of the first and second adhesive layers 2a', 2a" includes any one or two or more components, or both of the first and second adhesive layers 2a', 2a" include any one or two or more components. Furthermore, the first adhesive layer 2a' or the second adhesive layer 2a" may not include such components, and the constitution of the first adhesive layer 2a' or the second adhesive layer 2a" may be same or different each other.

However, the second adhesive layer 2a" may preferably include the nonionic surfactant, the alcohol, and the solubilizing agent in addition to the adhesive. Because these components are included in the second adhesive layer 2a" that contacts the skin when the matrix-type transdermal drug delivery system is adhered, the active component that is highly dissolved in the alcohol of the drug containing layer 2b slowly migrates toward the second adhesive layer 2a" which is near the skin, due to the concentration difference, and can be slowly dissolved in the alcohol with help of the solubilizing agent. The migration of the active component is promoted by the nonionic surfactant of the second adhesive layer 2a" and the active component can rapidly permeate the skin.

The nonionic surfactant and the alcohol may be included in the weight ratio of the nonionic surfactant to the alcohol of 1:1 to 1:4, in the adhesive layer. Because the skin permeation enhancers of the alcohol and the nonionic surfactant are included in the matrix layer, the skin permeability of the active component can be greatly improved according to the above-mentioned mechanism, and the medical efficacy maintaining time can be extended to 1 day or more, preferably to 3 days or more, and to a maximum of 7 days when the matrix-type transdermal drug delivery system is attached to the skin.

Furthermore, the first adhesive layer 2a', which is positioned between the drug containing layer 2b and the drug protecting layer 1 and does not contact the skin, may include only the adhesive, however, the first adhesive layer 2a' may also include the nonionic surfactant, the alcohol, and the solubilizing agent, preferably, in addition to the adhesive. With this, it is possible to further improve the skin permeability and the medical efficacy maintaining time of the active component.

In the above laminated structure of the matrix layer 2a', 2b, 2a", the first adhesive layer 2a' may include 20-75 wt % of the adhesive, 0-19.9 wt % of the nonionic surfactant, 0-29 wt % of the alcohol, and 0-19.9 wt % of the solubilizing agent, the drug containing layer 2b may include 0.1-25 wt % of the capsaicin or the capsaicin derivative, 0-15 wt % of the nonionic surfactant, 0-30 wt % of the alcohol having a molecular weight of 600 Daltons or less, and 0-20 wt % of the solubilizing agent including the hydrophilic polymer, and the second adhesive layer 2a" may include 20-75 wt % of the adhesive, 0-20 wt % of the nonionic surfactant, 0-29 wt % of the alcohol, and 0-19.9 wt % of the solubilizing agent, on the basis of the total weight of the first adhesive layer, the drug containing layer, and the second adhesive layer. At least one layer of the first and second adhesive layers 2a', 2a" may include the alcohol having a molecular weight of 600 Daltons or less, the nonionic surfactant, or the solubilizing agent including the hydrophilic polymer.

In the above laminated structure of the matrix layer 2a', 2b, 2a", for example, the first adhesive layer 2a' may include 20-75 wt % of the adhesive, 0-19.9 wt % of the nonionic surfactant, 0-29 wt % of the alcohol, and O-19.9 wt % of the solubilizing agent, the drug containing layer 2b may include 0.1-25 wt % of the capsaicin or the capsaicin derivative, 0-15 wt % of the nonionic surfactant, 1-30 wt % of the alcohol having a molecular weight of 600 daltons or less, and 0.1-20 wt % of the solubilizing agent including the hydrophilic polymer, and the second adhesive layer 2a" may include 20-75 wt % of the adhesive, 0.1-20 wt % of the nonionic surfactant, 0-29 wt % of the alcohol, and 0-19.9 wt % of the solubilizing agent, on the basis of the total weight of the matrix layer 2a', 2b, 2a".

In the above laminated structure of the matrix layer 2a', 2b, 2a", preferably, the first adhesive layer 2a' may include 20-75 wt % of the adhesive, 0.1-10 wt % of the nonionic surfactant, 0.1-15 wt % of the alcohol, and 0.1-5 wt % of the solubilizing agent, the drug containing layer 2b may include 0.1-25 wt % of the capsaicin or the capsaicin derivative, 0-5 wt % of the nonionic surfactant, 1-15 wt % of the alcohol having a molecular weight of 600 daltons or less, and 0.1-5 wt % of the solubilizing agent including the hydrophilic polymer, and the second adhesive layer 2a" may include 20-75 wt % of the adhesive, 0.1-10 wt % of the nonionic surfactant, 0.1-15 wt % of the alcohol, and 0.1-5 wt % of the solubilizing agent, on the basis of the total weight of the matrix layer 2a', 2b, 2a".

When the matrix layer 2a', 2b, 2a" includes the components separately in each layer with such concentration ratio, it is possible to further improve the skin permeability of the capsaicin or the capsaicin derivative, the active component, and it is also possible to extend the medical efficacy maintaining time greatly to 1 day or more, preferably to 3 days or more, and to a maximum of 7 days.

In the above laminated structure of the matrix layer 2a', 2b, 2a", preferably, the alcohol may be included in the first adhesive layer:the drug containing layer:the second adhesive layer in the weight ratio of 1:1-6:0.5-3, and preferably in the weight ratio of 1:3-4:1, and the nonionic surfactant may be included in the first adhesive layer:the drug containing layer:the second adhesive layer in the weight ratio of 1:0-1:0.5-2, and preferably in the weight ratio of 1:0:1. The solubilizing agent may be included in the first adhesive layer:the drug containing layer:the second adhesive layer in the weight ratio of 1:0-1:0.2-5, and preferably in the weight ratio of 3:1:3.

When the skin permeation enhancers of the alcohol and the nonionic surfactant, and the solubilizing agent, are separately included in each layer with such weight ratio, it is possible to include the capsaicin or the capsaicin derivative, the active component, in the drug containing layer 2b in high concentration, and it is also possible to maximize the skin permeability of the active component and to extend the medical efficacy maintaining time when the matrix-type transdermal drug delivery system is adhered to the skin due to the concentration difference and the solubility of the active component.

In the above laminated structure of the matrix layer 2a', 2b, 2a", the first adhesive layer 2a' may have a thickness of 10-60 μm, and the second adhesive layer 2a" may have a thickness of 10-120 μm. Furthermore, the total thickness of the first and second adhesive layers 2a', 2a" may be 30-300 μm, and is preferably 50-200 μm.

Furthermore, a preparation method of the matrix-type transdermal drug delivery system is provided according to this embodiment of the present invention.

The single layer matrix-type transdermal drug delivery system is prepared by steps of mixing the drug and the excipients uniformly, coating the same on the drug protecting layer 1, drying the same so as to form a single matrix layer, and then covering the release liner 3.

In the preparation method of the matrix-type transdermal drug delivery system having the laminated structure of two or more layers, an adhesive solution containing the adhesive including the water-insoluble acrylic polymer is separately coated on the drug protecting layer 1 and the release liner 3, first. In the coating step, the adhesive solution obtained by dissolving the adhesive component including the adhesive into an organic solvent of n-hexane, toluene, ethylacetate, and the like can be used, and the adhesive solution coated on at least one layer of the drug protecting layer 1 and the release liner 3 may further include the nonionic surfactant, the alcohol having a molecular weight of 600 Daltons or less, the solubilizing agent including the hydrophilic polymer, or all of the components together. In other words, it is possible to form the first adhesive layer 2a' or the second adhesive layer 2a" including any one or two or more components of the nonionic surfactant, the alcohol, or the solubilizing agent selectively in addition to the adhesive by carrying out the steps of coating the adhesive solution, and drying the same when necessary.

Furthermore, each adhesive solution coated on the drug protecting layer 1 and the release liner 3 is dried after carrying out the coating step. At this time, the organic solvent included in the adhesive solution can be evaporated and eliminated by drying the coated adhesive solution at a high temperature of 80-120° C. for a short time of 1-10 minutes. In this way, the first adhesive layer 2a' and the second adhesive layer 2a" are formed on the drug protecting layer 1 and the release liner 3, respectively.

The drying step can be carried out at a high temperature for a short time because the adhesive solution respectively coated on the drug protecting layer 1 and the release liner 3 does not include the active component of the capsaicin or the capsaicin derivative and there is no loss of the active component by evaporating in the drying step.

Furthermore, the drug containing layer 2b is prepared by coating the volatile component, which is the capsaicin or the capsaicin derivative, the solubilizing agent including the hydrophilic polymer, and the alcohol having a molecular weight of 600 Daltons or less on the first adhesive layer 2a' or the second adhesive layer 2a", after the drying step. The nonionic surfactant may be coated together therewith. Since the drying step is not carried out during the step of preparing the drug containing layer 2b, it is possible to easily manufacture the matrix-type transdermal drug delivery system including the capsaicin or the capsaicin derivative as the active component in a short time without a loss of the active component.

The coating step can be carried out by spraying the solution including the volatile component with a spray method, or by coating a fixed amount of the solution through a nozzle. At this time, the solution having viscosity that is suitable to carry out the coating step can be obtained by adequately adding the solubilizing agent including the hydrophilic polymer into a mixture solution of the active component of the capsaicin or the capsaicin derivative and the alcohol having a molecular weight of 600 Daltons or less (or the nonionic surfactant). Furthermore, the content of the active component and the drug containing layer 2b including the same can be controlled by adequately controlling the spraying time of the solution, the speed of the metering pump, the nozzle size, and the like, in the coating step.

After the coating step, the matrix-type transdermal drug delivery system can be finally prepared by forming the matrix layer including the first adhesive layer 2a', the drug containing layer 2b, and the second adhesive layer 2a", laminated in order, by adhering the first adhesive layer 2a' and the second adhesive layer 2a" to face each other.

As disclosed above, the skin permeability of the active component can be greatly improved and the medical efficacy maintaining time can be extended to 1 day or more, and to a maximum of 7 days, by formulating the capsaicin or the capsaicin derivative into the matrix-type transdermal drug delivery system of the present invention.

Therefore, the matrix-type transdermal drug delivery system of the present invention can be applied to a neuropathy treatment or a pain treatment requiring long-time medication and can make such long-time medication easy.

Furthermore, the economical mass production of the matrix-type transdermal drug delivery system is possible, because it is possible to produce the matrix-type transdermal drug delivery system including the active component more easily in a short time.

Hereinafter, the present invention is described in further detail through examples. However, the following examples are only for the understanding of the present invention and the present invention is not limited to or by them.

EXAMPLES 1-11

The matrix-type transdermal drug delivery system (the patch) is prepared by laminating the drug containing layer 2b between two adhesive layers 2a', 2a", according to the following method, and the component constitution of the matrix layer 2a', 2b, 2a" is disclosed in Tables 1 to 3.

An acrylate adhesive (National Starch & Duro-Tak, 87-2196, 87-4098, 87-4350, 87-2852, 87-2100) was introduced into a 50 ml sampling bottle, a skin permeation enhancer and a solubilizing agent disclosed in Tables 1 to 3 were further introduced therein so as to produce an adhesive solution, and then the solution was stirred at 200 rpm until the adhesive solution was completely uniform. The adhesive solution was stored for 10 minutes or more in order to eliminate bubbles.

The drug protecting layer 1 and the first adhesive layer 2a' were then prepared by coating the adhesive solution on the drug protecting film (Vilene nonwoven polyester, 3M nonwoven polyurethane 9905, 3M spunlaced nonwoven polyester 1538, 3M rayon nonwoven 1533, 3M rayon acetate) and drying the same at a high temperature of 80-120° C. for 8-12 minutes by using a "Lab coater and Dryer" (Swiss, Mathis Co.).

The release liner 3 and the second adhesive layer 2a" were prepared by coating the adhesive solution on the exfoliating film 3 (3M Scotchpak 9744, 1022, 3M paper release liner 1361, 9743) and drying the same at a high temperature of 80-120° C. for 8-12 minutes, in the same method.

Then, the skin permeation enhancer, the solubilizing agent, and the capsaicin (Taiwan, Formosa Laboratory) disclosed in Tables 1 to 3 were introduced into a 50 ml sampling bottle together and stirred at 200 rpm till the solution was completely uniform. The prepared solution was stored for 10 minutes or more in order to eliminate bubbles. The drug containing layer 2b was formed on the dried second adhesive layer 2a" by coating the solution with a nozzle.

The matrix-type transdermal drug delivery systems (the patches) of Examples 1-11 were finally prepared by forming the matrix layer including the first adhesive layer 2a', the drug containing layer 2b, and the second adhesive layer 2a" laminated in order by adhering the first adhesive layer 2a' and the second adhesive layer 2a" to face each other.

Figure 2:
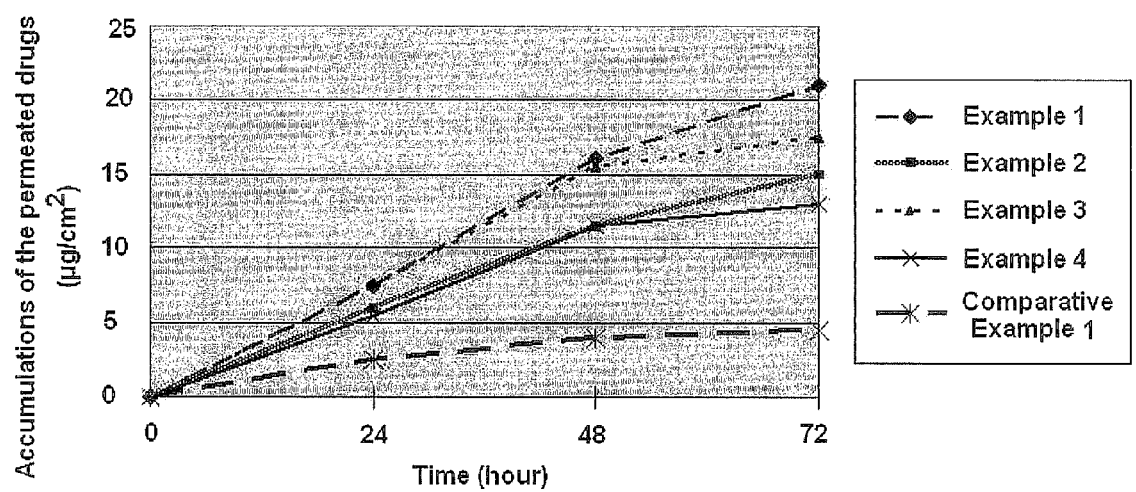
FIG. 2 is a graph representing accumulations of the permeated drugs with the passage of time when the matrix-type transdermal drug delivery system of Examples 1-4 and Comparative Example 1 are applied.
Figure 3:
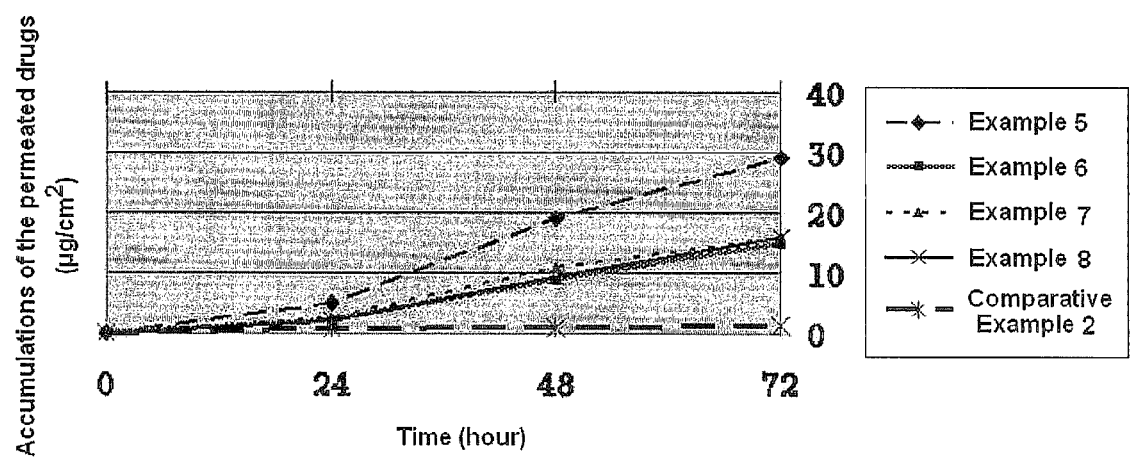
FIG. 3 is a graph representing accumulations of the permeated drugs with the passage of time when the matrix-type transdermal drug delivery system of Examples 5-8 and Comparative Example 2 are applied.

The patches of Examples 1-11 do not contain an extra membrane for release controlling of the active component. Hence, the only barrier for release controlling of the active component toward the skin may be the skin itself or the stratum corneum which is the upper part of the skin tissue. On the basis of the theory, therefore, drug (i.e. the capsaicin of the active component) penetrating tests were carried out to the skin of a dead human body (52 years old, male, Caucasian, the thigh part) by applying the Frantz Diffusion Cell automatic elution tester (U.S., Hanson Research Co.), which is well known to a person skilled in the related art, to the patches of Examples 1-11. The results of the tests are listed in Tables 1-3. In the results of the tests, the accumulations of the drugs penetrated into the skin with the passage of time are also illustrated in FIGS. 2 and 3. For reference, the testing results about the patches of Examples 1-4 are compared with Comparative Example 1 (a commercialized capsaicin ointment) in Table 1 and FIG. 2, the testing results about the patches of Examples 5-8 are compared with Comparative Example 2 in Table 2 and FIG. 3, and the testing results about the patches of Examples 9-11 are compared with Comparative Example 3 in Table 3.

For reference, the commercialized capsaicin ointments of Comparative Examples 1-3 were applied 4 times a day, every 6 hours, according to the operating manual, and the concentration of the capsaicin derivative used was 10-40 ug/cm$^2$ which is the concentration recommended by German monograph, "Capsicum", 1990.

TABLE 1

| | Component constitution of the matrix layer (wt %) | | | | | | |
|---|---|---|---|---|---|---|---|
| | Active component | Adhesive | Other components (skin permeation enhancer, solubilizing agent) | | | | Drug |
| Classification | Capsaicin USP | DT 87-2852 | Propylene glycol | Span 20 ® | Polyvinyl-pyrrolidone | Colloidal silicone dioxide | penetrating amount (ug/cm$^2$ · 3 day) |
| Example 1 | 6.7 | 66.6 | 15.5 | 6.5 | 3.2 | 1.5 | 21.1 |
| Example 2 | 0.6 | 68.1 | 20.1 | 6.0 | 4.2 | 1.0 | 14.9 |
| Example 3 | 12.5 | 74.7 | 5.4 | 1.8 | 5.1 | 0.5 | 17.9 |
| Example 4 | 1.0 | 80.5 | 10.5 | 3.5 | 2.0 | 2.5 | 13.4 |
| Comparative Example 1 | Commercialized capsaicin ointment (0.075% content ointment) | | | | | | 4.3 |

In Table 1, the other components are separately distributed in the first adhesive layer:the drug containing layer:the second adhesive layer, as the following weight ratio in order, the adhesive of 1:0:1, propylene glycol of 1:3:1, Span 20® of 1:0:1, polyvinylpyrrolidone of 2:1:2, and colloidal silicone dioxide of 3:1:3.

TABLE 2

Component constitution of the matrix layer (wt %)

| Classification | Active component Capsaicin USP | Adhesive DT 87-2852 | Propylene glycol | Sorbitan monooleate | Polyvinyl-pyrrolidone | Colloidal silicone dioxide | Drug penetrating amount (ug/cm² · 3 day) |
|---|---|---|---|---|---|---|---|
| Example 5 | 0.6 | 67.0 | 20.6 | 6.3 | 5.3 | 0.2 | 29.1 |
| Example 6 | 4.3 | 66.0 | 19.5 | 5.0 | 4.2 | 1.0 | 15.1 |
| Example 7 | 2.0 | 70.0 | 5.0 | 10.0 | 10 | 3 | 16.3 |
| Example 8 | 1.0 | 75.0 | 10.5 | 8.5 | 2.5 | 2.5 | 16.5 |
| Comparative Example 2 | Commercialized capsaicin ointment, Diaxen (0.075% content ointment, Korea) | | | | | | 2.5 |

In Table 2, the other components are separately distributed in the first adhesive layer:the drug containing layer:the second adhesive layer, as following weight ratio in order, the adhesive of 1:0:1, propylene glycol of 1:4:1, sorbitan monooleate of 1:0:1, polyvinylpyrrolidone of 3:1:3, and colloidal silicone dioxide of 2:1:2.

TABLE 3

Component constitution of the matrix layer (wt %)

| Classification | Active component Capsaicin USP | Adhesive DT 87-2852 | Propylene glycol | Sorbitan monooleate | Polyvinyl-pyrrolidone | Colloidal silicone dioxide | Drug penetrating amount (ug/cm² · 3 day) |
|---|---|---|---|---|---|---|---|
| Example 9 | 6.7 | 82.1 | 3 | 3.5 | 3.2 | 1.5 | 5.6 |
| Example 10 | 4.3 | 71.0 | 19.5 | 0 | 4.2 | 1.0 | 9.5 |
| Example 11 | 1.1 | 66.5 | 20.4 | 6.5 | 5.4 | 0.1 | 11.9 |
| Comparative Example 3 | Commercialized capsaicin ointment (0.075% content ointment) | | | | | | 3.7 |

| | Capsaicin USP | DT 87-2852 | Menthol | Sorbitan monooleate | Polyvinyl-pyrrolidone | Colloidal silicone dioxide | |
|---|---|---|---|---|---|---|---|
| Comparative Example 4 | 12.5 | 60 | 2.5 | 20 | 5 | 0 | 1.5 |

In Table 3, the other components of Example 9 are separately distributed in the first adhesive layer:the drug containing layer:the second adhesive layer, as the following weight ratio in order, the adhesive of 1:0:1, propylene glycol of 0:1:0, sorbitan monooleate of 1:0:0, polyvinylpyrrolidone of 2:1:2, and colloidal silicone dioxide of 3:1:3. The other components of Example 10 are separately distributed in the first adhesive layer:the drug containing layer:the second adhesive layer, as the following weight ratio in order, the adhesive of 1:0:1, propylene glycol of 1:4:1, sorbitan monooleate of 0:0:0, polyvinylpyrrolidone of 3:1:3, colloidal silicone dioxide of 2:1:2. Further, all of the other components of Example 11 are distributed in the single matrix layer which is not a laminated structure. Comparative Example 4 was prepared by the component constitution that is used for an ordinary matrix-type transdermal drug delivery system.

Referring to Tables 1-3, it is indicated that the patches of Examples 1-11 show largely improved skin permeability of the active component, i.e., the drug penetrating amount, in comparison with Comparative Examples 1-4. It is also known that the drug penetrating amount is improved still more in the case of including the other components separately in each layer. Furthermore, referring to FIGS. 2 and 3, it is also indicated that the accumulation of the drug penetrated into the skin is largely increased with the passage of time by adhering the patches of Examples 1-8, in comparison with Comparative Examples 1-4, and the medical efficacy maintaining time is largely increased.

What is claimed is:

1. A matrix-type transdermal drug delivery system, comprising:
    a drug protecting layer;
    a first adhesive layer that is formed on the drug protecting layer and comprises 20-75 wt % of an adhesive comprising a water-insoluble acrylic polymer, 0.1-10 wt % of a nonionic surfactant, 0.1-15 wt % of an alcohol having a molecular weight of 600 Daltons or less, and 0.1-5 wt % of a solubilizing agent comprising a hydrophilic polymer said first adhesive layer absent an active component;
    a drug containing layer that is formed on the first adhesive layer and comprises 0.1-25 wt % of one material or a mixture of two or more materials selected from the group consisting of capsaicin, dihydrocapsaicin, nordihydrocapsaicin, homodihydrocapsaicin, homocapsaicin, capsazepine, N-vanillylnonanamide, (Z)-capsaicin, (E)-capsaicin, and 6-iodonordihydrocapsaicin, 0-5 wt % of a nonionic surfactant, 1-15 wt % of an alcohol having a molecular weight of 600 Daltons or less, and 0.1-5 wt % of a solubilizing agent comprising a hydrophilic polymer;

a second adhesive layer that is formed on the drug containing layer and comprises 20-75 wt % of an adhesive including a water-insoluble acrylic polymer, 0.1-10 wt % of a nonionic surfactant, 0.1-15 wt % of an alcohol having a molecular weight of 600 Daltons or less, and 0.1-5 wt % of a solubilizing agent comprising a hydrophilic polymer said second adhesive layer absent an active component; and a release liner formed on the second adhesive layer, wherein the concentrations of the components are based on the total weight of the first adhesive layer, the drug containing layer, and the second adhesive layer, wherein the alcohol in the first adhesive layer, the drug containing layer, and the second adhesive layer is present in a weight ratio of 1:1-6:0.5-3 respectively, wherein the nonionic surfactant in the first adhesive layer, the drug containing layer, and the second adhesive layer is present in a weight ratio of 1:0-1:0.5-2 respectively, wherein the solubilizing agent in the first adhesive layer, the drug containing layer, and the second adhesive layer is present in a weight ratio of 1:0.1-1:0.2-5 respectively, and wherein said first adhesive layer, drug containing matrix layer and second adhesive layer are laminated in order.

2. The matrix-type transdermal drug delivery system according claim 1, wherein the water-insoluble acrylic polymer comprises a homopolymer or a copolymer polymerized from one or more monomers selected from the group consisting of 2-ethylhexylacrylate, vinylacrylate, and vinylacrylic acid.

3. The matrix-type transdermal drug delivery system according to claim 1, wherein the alcohol comprises a material or a mixture of two or more materials selected from the group consisting of ethanol, isopropanol, butanol, benzylalcohol, triacetin, transcutol, propyleneglycol, glycerin, and a polyethyleneglycol having a molecular weight of 600 Daltons or less.

4. The matrix-type transdermal drug delivery system according to claim 1, wherein the nonionic surfactant comprises a material or a mixture of two or more materials selected from the group consisting of glycerol monolaurate, glycerol monooleate, glycerol monolinoleate, glycerol trilaurate, glycerol trioleate, glycerol tricaprylate, propylene glycol monolaurate, propylene glycol dilaurate, caprylic/capric triglyceride, methyl laurate, methyl caprate, isopropyl myristate, isopropyl palmitate, ethyl oleate, oleyl oleate, sorbitan monolaurate, sorbitan monooleate, polyoxyethylene lauryl ether, polyoxyethylene cetyl ether, polyoxyethylene stearyl ether, polyoxyethylene oleyl ether, polyoxyethylene stearate, polyoxyethylene-9-nonyl phenyl ether, polyethyleneglycol-40 hydrogenated caster oil, polyethyleneglycol-35 hydrogenated caster oil, octocynol-11, a fatty acid ester of Tween, and a fatty acid ester of sorbitan.

5. The matrix-type transdermal drug delivery system according to claim 1, wherein the hydrophilic polymer comprises a material or a mixture of two or more materials selected from the group consisting of a polyvinylpyrrolidone a polyvinylalcohol, a sodium carboxymethyl cellulose, a hydroxyethyl cellulose, a hydroxypropyl cellulose, a hydroxypropyl methyl cellulose, a carbopol, and a poloxamer.

6. The matrix-type transdermal drug delivery system according to claim 1, wherein the drug protecting layer comprises a film or a nonwoven fabric consisting of polyester, polyurethane, polyethylene, or rayon.

7. The matrix-type transdermal drug delivery system according to claim 1, wherein the alcohol is comprised in the first adhesive layer, the drug containing layer, and the second adhesive layer in a weight ratio of 1:3-4:1.

8. The matrix-type transdermal drug delivery system according to claim 1, wherein the nonionic surfactant is comprised in the first adhesive layer, the drug containing layer, and the second adhesive layer in a weight ratio of 1:0:1.

9. The matrix-type transdermal drug delivery system according to claim 1, wherein the solubilizing agent is comprised in the first adhesive layer, the drug containing layer, and the second adhesive layer in a weight ratio of 3:1:3.

10. A preparation method of the matrix-type transdermal drug delivery system of claim 1, comprising:
   coating an adhesive solution containing an adhesive comprising a water-insoluble acrylic polymer on a drug protecting layer and a release liner, separately;
   drying the coated adhesive solution;
   coating capsaicin or a capsaicin derivative, a solubilizing agent comprising a hydrophilic polymer, and an alcohol having a molecular weight of 600 Daltons or less on the adhesive solution that is coated on the drug protecting layer and the release liner; and adhering the drug protecting layer and the release liner to face the sides on which the adhesive solutions are coated to each other.

11. The preparation method of the matrix-type transdermal drug delivery system according to claim 10, wherein an adhesive solution further comprising a nonionic surfactant, an alcohol having a molecular weight of 600 Daltons or less, or a mixture thereof is coated on at least one of the drug protecting layer and the release liner.

12. The preparation method of the matrix-type transdermal drug delivery system according to any one of claims 10 and 11, wherein an adhesive solution further comprising a solubilizing agent including a hydrophilic polymer is coated on at least one of the drug protecting layer and the release liner.

13. The preparation method of the matrix-type transdermal drug delivery system according to claim 12, wherein an adhesive solution comprising the adhesive, the nonionic surfactant, the alcohol, and the solubilizing agent is coated on the release liner.

14. The preparation method of the matrix-type transdermal drug delivery system according to claim 13, wherein an adhesive solution comprising the adhesive, the nonionic surfactant, the alcohol, and the solubilizing agent is coated on the drug protecting layer.

15. The matrix-type transdermal drug delivery system according to claim 1, wherein the solubilizing agent further comprises a colloidal silicone dioxide.

* * * * *